(12) United States Patent
Bonrath et al.

(10) Patent No.: US 6,949,685 B2
(45) Date of Patent: Sep. 27, 2005

(54) ETHYNYLATION PROCESS

(76) Inventors: Werner Bonrath, 29 Luckenbachweg, D-79115 Freiburg (DE); Bernd Englert, 59 Schoenerwerderstrasse, CH-5036 Oberentfelden (CH); Reinhard Karge, 3 Belchenring, D-79219 Staufen (DE); Michael Schneider, 3A Doermattweg, CH-5070 Frick (CH)

( * ) Notice: Subject to any disclaimer, the term of this patent is extended or adjusted under 35 U.S.C. 154(b) by 0 days.

(21) Appl. No.: 10/489,523

(22) PCT Filed: Sep. 19, 2002

(86) PCT No.: PCT/EP02/10508

§ 371 (c)(1),
(2), (4) Date: Oct. 15, 2004

(87) PCT Pub. No.: WO03/029175

PCT Pub. Date: Apr. 10, 2003

(65) Prior Publication Data

US 2005/0059844 A1 Mar. 17, 2005

(30) Foreign Application Priority Data

Sep. 28, 2001 (EP) .............................. 01123492

(51) Int. Cl.$^7$ ............... C07C 33/042; C07C 33/04; C07C 33/044; C07C 33/046
(52) U.S. Cl. ............................ 568/874; 568/873
(58) Field of Search .................... 568/873, 874

(56) References Cited

U.S. PATENT DOCUMENTS 3,801,653 A    4/1974   Pasedach et al.

FOREIGN PATENT DOCUMENTS

DE    2 018 971       11/1971
EP    0 982 282 A2    3/2000

*Primary Examiner*—Elvis O. Price
(74) *Attorney, Agent, or Firm*—Bryan Cave LLP

(57) ABSTRACT

A process for the manufacture of an acetylenically unsaturated alcohol comprising reacting formaldehyde, an aldehyde or a ketone (a carbonyl compound) with acetylene in the presence of ammonia and a strongly basic macroporous anion exchange resin, the latter preferably featuring a polystyrene matrix and quaternary ammonium groups, preferably of type I or Type II. The reaction products, which depending on the starting carbonyl compound are propargyl alcohol or 1-monosubstituted or 1,1-disubstituted derivatives thereof, are of use as intermediates in the synthesis of many useful end products, inter alia in the field of vitamins and carotenoids.

17 Claims, 1 Drawing Sheet

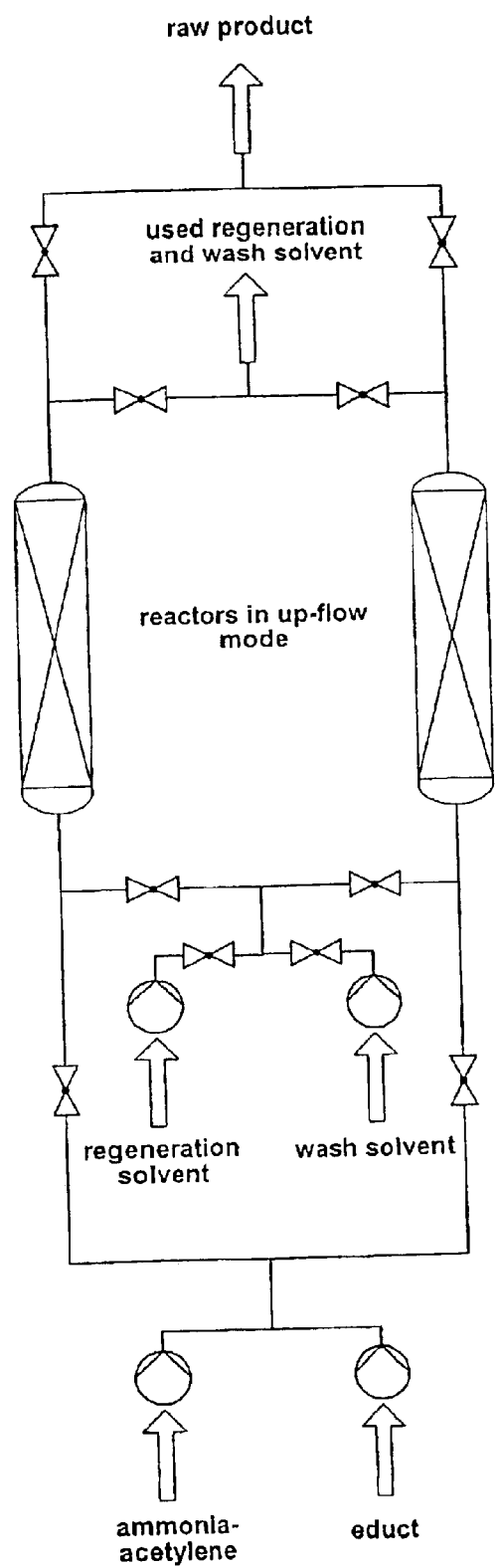
Figure

ETHYNYLATION PROCESS

This application is the National Stage of International Application No. PCT/EP02/10508, filed Sep. 19, 2002.

The present invention relates to an ethynylation process. More particularly, the present invention relates to a process for the manufacture of acetylenically unsaturated alcohols (propargyl alcohol or 1-monosubstituted or 1,1-disubstituted derivatives thereof, depending on the nature of the starting material to be ethynylated), in which process formaldehyde, an aldehyde other than formaldehyde, or a ketone, each of these being referred to hereinafter in general as a "carbonyl compound", is reacted with acetylene (ethyne) in the presence of ammonia and a strongly basic macroporous anion exchange resin. The reaction products are of use as intermediates in the synthesis of many useful end products, inter alia in the field of vitamins and carotenoids. For example, one such useful intermediate is dehydrolinalool, which itself can be converted via citral to β-ionone and isophytol, themselves being known starting materials for vitamin A and vitamin E, respectively.

The manufacture of acetylenically unsaturated alcohols by the reaction of a carbonyl compound with acetylene in the presence of ammonia and an anion exchange resin containing quaternary ammonium groups, e.g. AMBERLITE® IRA 400 (a "gel" type), is known for example from German Offenlegungsschrift 2 018 971. However, this process suffers by featuring an unsatisfactory rate of reaction, expressed in terms of the "space-time-yield" (also referred to as liquid hourly space velocity, LHSV, being the ratio of the volume of the reaction mixture passed per hour over the catalyst to the volume of the catalyst in the reactor).

It has now been found that by using a strongly basic macroporous anion exchange resin instead of the anion exchange resin of the "gel" type used hitherto as the catalyst in the ethynylation of carbonyl compounds a superior LHSV is achieved.

Accordingly, the present invention is a process for the manufacture of an acetylenically unsaturated alcohol comprising reacting formaldehyde, an aldehyde or a ketone (a carbonyl compound) with acetylene in the presence of ammonia and a strongly basic macroporous anion exchange resin.

The expression "strongly basic anion exchange resin" is well known in the art of ion exchange, and many useful review articles concern ion exchangers, inter alia strongly basic anion exchange resins: see for example Ullmann's Encyclopedia of Industrial Chemistry, Vol. A 14 (1989), "Ion Exchangers" on pages 393–459, of which pages 397–400 are particularly pertinent for the aspects "strongly basic" and "macroporosity" (degree of crosslinking) for anion exchange resins. In general, ion exchange resins featuring quaternary ammonium groups are strongly basic, and both "type I (or 1)" such resins, featuring benzyltrimethylammonium groups and being strongly basic, and "type II (or 2)" such resins, featuring benzyldimethylethanolammonium groups and being slightly less basic, but sufficiently strongly basic, are suitable for use in the process of the present invention, provided they are also "macroporous". The latter term as used herein denotes any resin which has a higher degree of cross-linking than a gel resin (such as AMBERLITE® IRA 400). The pore diameter in a typical macroporous resin is about 100 nm as compared to about 1 nm in a gel resin: see, besides Ullmann's Encyclopedia of Industrial Chemistry (1989), Vol A 14, pp. 399–400, DIN 54 400, "Ionenaustausch-Begriffe", 1987, p. 7. Apart from the many sources of information in the scientific literature, the catalogues of suppliers of ion exchangers categorize their products appropriately such that selecting a "strongly basic macroporous anion exchange resin" for use in the process of the present invention does not pose a problem.

For the purpose of the present invention, the preferred strongly basic macroporous anion exchange resins are those featuring a polystyrene matrix with quaternary amnonium cations and hydroxyl anions, particularly AMBERSEP® 900 OH, as supplied by Rohm & Haas Deutschland GmbH, Frankfurt/Main, Germany, and CTA 505, as supplied by Purolite (representative: Staerkle & Nagler A G, Zürich, Switzerland). Further examples of suitable strongly basic macroporous anion exchange resins are AMBERLITE® IRA 900 (Rohm & Haas) and DOWEX® MSA-1, Diaion HPA25 and PA 308 (all Dow Chemical). Strongly basic macroporous anion exchange resins featuring a polyacrylic matrix rather than a polystyrene matrix can be used in the process of the present invention, but, as indicated above, are less preferred than those with a polystyrene matrix.

The simplest carbonyl compound which can be reacted with acetylene in accordance with the process of the present invention is formaldehyde, $H_2CO$, the product being propargyl alcohol, $HC\equiv CCH_2OH$.

The nature of the aldehyde or ketone which can be reacted with acetylene in accordance with the process of the present invention is not critical, and any aldehyde or ketone which is known to react with acetylene to form an acetylenically unsaturated alcohol may be used, i.e. according to the equation,

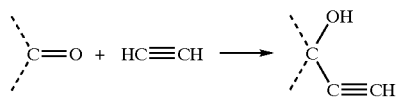

the unspecified moieties borne by the "central" carbon atom being those featured in known aldehydes and ketones or in further aldehydes and ketones which can be produced analogously to the known ones, Thus, for example, the aldehyde, including formaldehyde, or ketone may be one of those of formula "$R^5$—CO—$R^6$" as defined in German Offenlegungsschrift 2 018 971, of which the contents are incorporated herein for this purpose. Preferably, the starting carbonyl compound is a ketone of the general formula $$R^1-CH_2-CO-CH_2-R^2 \qquad I$$

wherein each of $R^1$ and $R^2$, independently, signifies hydrogen, alkyl, alkenyl, cycloalkyl-alkyl, cycloalkly-alkenyl, cycloalkenyl-alkyl or cycloalkenyl-alkenyl, each of the last four mentioned groups being optionally substituted on its cycloalkyl or cycloalkenyl ring, as appropriate, by one to three methyl or ethyl groups, and the total number of carbon atoms, including those of the —$CH_2$—CO—$CH_2$ moiety, not exceeding 40.

In the above definition of the ketones of the general formula I an alkyl group signified by $R^1$ and/or $R^2$ can contain up to 22 carbon atoms and may be straight chain or branched, which also applies to the aLkenyl group. Said alkenyl group, in addition, may feature up to 4 double bonds. The cycloalkyl-alkyl, cycloalkenyl-alkyl, cycloalkyl-alkenyl or cycloalkenyl-alkenyl group signified by $R^1$ and/or $R^2$ features a cycloalkyl or cycloalkenyl ring, as appropriate, which has from 5 to 12 ring members; the alkyl or alkenyl part of such group can contain from 1 to 8 carbon atoms and be straight chain or branched, and in the case of alkenyl as part of such group this can feature up to 4 double bonds. Furthermore, and as also indicated in the definition of formula I, the cycloalkyl or cycloalkenyl ring part of such groups is either unsubstituted or is substituted by one, two or three methyl or ethyl groups, whereby in the case of di- or trisubstitution the substituents can be the same (methyl or ethyl) or different (a mixture of methyl and ethyl substituents). A particularly preferred optionally substituted cycloalkenyl group (as part of cycloalkenyl-alkyl or cycloalkenyl-alkenyl) is the well known 2,6,6-trimethyl-1-cyclohexen-1-yl group.

Clearly, the total number of carbon atoms, including any ring methyl or ethyl substituents, if appropriate, of either $R^1$ or $R^2$ is limited by that of the remaining $R^2$ or $R^1$, respectively, to satisfy the criterion of the molecule $R^1$—$CH_2$—$CO$—$CH_2$—$R^1$ as a whole containing a maximum of 40 carbon atoms.

Of particular interest is the process of the present invention when applied to the ethynylation of methyl ethyl ketone, 6-methyl-5-hepten-2-one, 6-ethyl 5-octen-2-one, hexahydropseudoionone (6,10-dimethyl-2-undecanone), 4-(2,6,6-trimethyl-1-cyclohexen-1-yl)-3-buten-2-one and 6,10,14-trimnethyl-2-pentadecanone (all ketones of formula I), and also to the ethynylation of methylglycol dimethyl acetate [$CH_3COCH(OCH_3)_2$], not a ketone of the formula I, but nonetheless a ketone amongst many others which can be reacted with acetylene in accordance with the process of the present invention. Of these specifically named ketones 6-methyl-5-hepten-2-one is a particularly preferred ketone which can be reacted with acetylene by the process of the present invention; the product in this case is dehydrolinalool.

The ammonia used as the solvent in the process of the present invention is maintained in the liquid state by appropriate choice of temperature and pressure, the reaction temperature conveniently being in the range from about 0° C. to about 40° C. and the pressure being at an appropriate value, depending on the reaction temperature, from about 10 to about 20 bar (about 1 MPa to about 2 MPa). By using liquefied ammonia as the reaction solvent, the process of the present invention avoids the use of organic solvents, which is one of its advantages.

The reaction temperature is preferably from about 10° C. to about 30° C., more preferably from about 12° C. to about 20° C.

The molar ratio of the acetylene to the formaldehyde, aldehyde or ketone (carbonyl compound), e.g. a ketone of the formula I, in the reaction mixture for carrying out the process of the present invention is generally in the range from about 2.5:1 to about 3.5 to 1. Furthermore, the molar ratio of ammonia to carbonyl compound in said process is generally from about 10:1 to about 20:1, preferably from about 12:1 to about 15:1.

The process of the present invention can be carried out in a manner known per se for the ethynylation of carbonyl compounds. Typically, a solution of acetylene in ammonia and, separately, the formaldehyde, aldehyde or ketone are introduced into a reactor, or into parallel reactors, filled with the strongly basic macroporous anion exchange resin, whereupon the reaction takes place at the selected temperature and pressure.

The (each) reactor is conveniently a fixed bed reactor. Conventionally the reactor system as a whole features means for regenerating the catalyst and for recycling the ammonia solvent and excess, unreacted starting materials acetylene and carbonyl compound.

It has been found that under favourable reaction conditions the reactor can be operated continuously for more than 1000 hours with about 5 regenerations of the catalyst, For carrying out the ethynylation process of the present invention as a continuous process, two or more reactors can be operated in parallel, thus allowing the ethynylation process to proceed in one or more reactors while the resin in the other (further) reactor(s) is regenerated. As an alternative, two or more reactors may be connected in series in order to promote a more complete conversion of the carbonyl compound to the acetylenically unsaturated alcohol. A diagrammatic representation of such a reactor and regeneration system is given in the accompanying Figure.

The regeneration of the catalyst can be effected for example by rinsing with about 3–10 wt. %, preferably about 4–6 wt. %, methanolic alkali hydroxide, e.g. potassium hydroxide, followed by rinsing with methanol for removal of the alkali. The necessary frequency of regeneration of the catalyst depends on the particular catalyst, the reaction parameters and the requirements as to the purity of the desired product, and can be determined by monitoring the composition of the reaction product as it evolves.

The process of the present invention embraces as a further aspect the above-described post-reaction regeneration of the catalyst.

Besides providing superior space-time-yields the process of the present invention avoids the use of organic solvents in the ethynylation reaction, proceeds at relatively low reaction temperatures and pressure, and permits long reaction cycles through extended catalyst life time by frequent regeneration of the catalyst.

The invention is illustrated by the following Example:

EXAMPLE

A reactor system comprising two serially connected tubular reactors with an inner diameter of 2.8 cm and a length of 117.6 cm and having an overall reactor volume of 1.45 l was used. Each reactor was charged with 334 g (approx. 1.2 l) of the catalyst AMBERSEP® 900 OH, which had been pretreated by rinsing with deionized water until the eluate reached pH 7, and thereafter washed with methanol for removal of water and with 6-methyl-5-hepten-2-one ("methylheptenone") for removal of methanol. Finally, excess methylheptenone was drained from the catalyst.

Acetylene was dissolved in ammonia at 6° C. and 9 bar (0.9 MPa) resulting in a mixture that contained approximately 24 wt. % of acetylene in the liquid phase. This mixture was introduced up-flow at a rate of 1.6 kg/h into the reactor system. Simultaneously, methylheptenone was introduced up-flow at a rate of 0.78 l/h (approx. 0.67 kg/h) into the reactor system. The temperature in the reactor tubes was maintained at 15–18° C. and the pressure was adjusted to 12 bar (1.2 MPa).

The crude product leaving the reactor was divided in a heated separator at 78° C. into fractions containing the desired reaction product, i.e. dehydrolinalool (DLL), and the ammonia-acetylene-mixture, the latter being subsequently recycled.

Approximately 500 g to 540 g of DLL per litre reactor volume and hour were obtained after 1000 hours in this continuous process, the yield corresponding to an LHSV of about 2.87 $h^{-1}$.

The average product composition was 96.4 area % according to gas chromatography [GC-area %] of DLL, 1.17 GC-area % of methylheptenone and 0.34 GC-area % of diol by product.

The catalyst could be regenerated by temporarily interrupting the continuous production by discontinuing the introduction of the acetylene-ammonia mixture in order to allow the catalyst to then be rinsed with methylheptenone, then discontinuing the methylheptenone introduction and instead submitting the catalyst to the passage of methanol containing 5 wt. % of potassium hydroxide at a rate of 0.25 l/h for 19.2 hours (total 4.8 l), stopping the passage of this alkaline methanol and washing the catalyst instead with methanol as such at a rate of 0.25 l/h for a further 19.2 hours (total 4.8 l), and finally reestablishing the simultaneous introduction of the acetylene-ammonia mixture and the methylheptenone.

What is claimed is:

1. A process for the manufacture of all acetylenically unsaturated alcohol comprising reacting formaldehyde, an aldehyde or a ketone (a carbonyl compound) with acetylene in the presence of ammonia and a strongly basic macroporous anion exchange resin.

2. A process according to claim 1, wherein the anion exchange resin is one featuring a polystyrene matrix and quaternary ammonium groups.

3. A process according to claim 1 wherein the anion exchange resin is AMBERSEP® 900 OH, CTA 505, AMBERLITE® IRA 900, DOWEX® MSA-1, Diaion HPA25 or PA 308.

4. A process according to claim 1, wherein the carbonyl compound is a ketone of the general formula $$R^1-CH_2-CO-CH_2-R^2$$

wherein each of $R^1$ and $R^2$, independently, signifies hydrogen, alkyl, alkenyl, cycloalkyl-alkyl, cycloalkyl-alkenyl, cycloalkenyl-alkyl or cycloalkenyl-alkenyl, each of the last four mentioned groups being optionally substituted on its cycloalkyl or cycloalkenyl ring, as appropriate, by one to three methyl or ethyl groups, and the total number of carbon atoms, including those of the $-CH_2-CO-CH_2-$ moiety, not exceeding 40.

5. A process according to claim 1 wherein the ketone is methyl ethyl ketone, methylglyoxal dimethyl acetal, 6-methyl-5-hepten-2-one, 6-ethyl-5-octen-2-one, hexahydropseudoionone, 4-(2,6,6-trimethyl-1-cyclohexen-1-yl)-3-buten-2-one or 6,10,14-trimethyl-2-pentadecanone.

6. A process according to claim 5, wherein the ketone is 6-methyl-5-hepten-2-one and the product is dehydrolinalool.

7. A process according to claim 1, wherein the molar ratio of acetylene to the carbonyl compound is from about 2.5:1 to about 3.5:1.

8. A process according to claim 1, wherein the molar ratio of ammonia to the carbonyl compound is from about 10:1 to 20:1.

9. A process according to claim 1, wherein the reaction temperature is in the range from 0° C. to 40° C., and the pressure is at an appropriate value, depending on the reaction temperature, from 10 to 20 bar (1 MPa to 2 MPa) to maintain the ammonia in the liquefied state.

10. A process according to claim 1, wherein the reaction is carried out in a reactor system which as a whole features means for regenerating the catalyst, the regeneration of the catalyst being effected by rinsing with 3–10 wt. %, methanolic alkali hydroxide, followed by rinsing with methanol for removal of the alkali.

11. A process according to claim 2, wherein the anion exchange resin is type I or type II.

12. A process according to claim 1, wherein the molar ratio of ammonia to the carbonyl compound is from about 12:1 to about 15:1.

13. A process according to claim 9, wherein the reaction temperature is in the range from about 10° C. about 30° C.

14. A process according to claim 9, wherein the reaction temperature is in the range from about 12° C. to about 20° C.

15. A process according to claim 10, wherein the regeneration of the catalyst is effected by rinsing with 4–6% wt. % of methanolic alkali hydroxide.

16. A process according to claim 10, wherein the methanolic alkali hydroxide is potassium hydroxide.

17. A process according to claim 15, wherein the methanolic alkali hydroxide is potassium hydroxide.

* * * * *